United States Patent [19]

Nakajima et al.

[11] 4,399,022

[45] Aug. 16, 1983

[54] REFERENCE ELECTRODE FOR OXYGEN PROBE

[75] Inventors: Yoshio Nakajima, Hiroshima; Takaharu Moriya; Hajime Nakamura, both of Kure; Koji Omosako, Hiroshima; Yoshio Tokuta, Kure, all of Japan

[73] Assignee: Nisshin Steel Company, Ltd., Tokyo, Japan

[21] Appl. No.: 353,815

[22] Filed: Mar. 2, 1982

[30] Foreign Application Priority Data

Mar. 26, 1981 [JP] Japan ............................ 56-44327

[51] Int. Cl.$^3$ ............................................ G01N 27/58
[52] U.S. Cl. ................................. 204/422; 436/2; 436/8; 436/19
[58] Field of Search ............... 204/195 S, 1 S, 422, 204/423, 421, 424; 436/2, 136, 137, 8, 19; 422/98

[56] References Cited

U.S. PATENT DOCUMENTS 4,155,828  5/1979  Takao et al. .................. 204/195 S

FOREIGN PATENT DOCUMENTS 2819381  11/1979  Fed. Rep. of Germany ... 204/195 S

Primary Examiner—G. L. Kaplan
Attorney, Agent, or Firm—Webb, Burden, Robinson & Webb

[57] ABSTRACT

In the reference electrode for the oxygen probe comprising a mixture of Cr powder and $Cr_2O_3$ powder, an improved reference electrode characterized in that Cr powder and $Cr_2O_3$ powder are mixed in a ratio 97%:3% to 80%:20% and the mixture is sintered beforehand. An oxygen probe using this electrode exhibits improved response, stability and reproducibility in molten steel.

10 Claims, 7 Drawing Figures

REFERENCE ELECTRODE FOR OXYGEN PROBE

TECHNICAL FIELD OF THE INVENTION

This invention relates to a novel reference electrode for oxygen probes which has improved response, stability and reproducibility when the activity of oxygen in molten steel is measured.

BACKGROUND OF THE INVENTION

In recent years requirements for the quality of steel materials have become stricter and stricter, and the need to save energy and to economize on labor has increased. Thus, continuous casting now accounts for a large proportion of the steel production, and in connection with this trend, the monitoring and control of molten steel has become far more important. In the monitoring of molten steel, one of the most important factors is the activity of oxygen in molten steel. And it is well known that success in the measurement thereof has a great influence upon the subsequent steelmaking process.

Accordingly, the oxygen probe which determines the activity of oxygen in molten steel by means of the electromotive force of a concentration cell has been developed and is commercially available.

Although the known oxygen probe is protected with a high quality refractory material, the allowable immersion time is limited when it is directly dipped in molten steel. Therefore, in order to determine oxygen activity correctly it is necessary for an oxygen probe that its electromotive force (hereinafter simply referred to as "emf") be stabilized within the allowable immersion time, and that the stabilized state be maintained without disruption for a period of time. Also it must exhibit good reproducibility in order to secure the determined values with reliability.

However, the known oxygen probes have a disadvantage in that they must be immersed for a long time before the caused emf is stabilized, or the emf fluctuates after the response time has passed, that is, they are inadequate in response and stability. Also they are not satisfactory in reproducibility either, and therefore they are not yet practically used in production lines in steelmaking plants.

Therefore, there has been a demand for an improved oxygen probe which has improved response, stability and reproducibility and thus is satisfactory for use in actual production lines.

However, we do not know of any report which discusses and analyzes the above-mentioned defects of the conventional oxygen probes, and suggests measures for improvement thereof. We have noted that the factor which has the most important influence on response, stability and reproducibility is the reference electrode, and tried to improve the reference electrode and completed this invention.

DISCLOSURE OF THE INVENTION

According to this invention, in the reference electrode for the oxygen probe comprising a mixture of Cr powder and $Cr_2O_3$ powder there is provided an improved reference electrode which is characterized in that Cr powder and $Cr_2O_3$ powder are mixed in a ratio 97%:3% to 80%:20% by weight, and the mixture is sintered at a temperature not lower than 1550° C. in an oxygen-free atmosphere and is pulverized again.

Preferably the $Cr-Cr_2O_3$ mixture is filled in the electrolyte tube in an amount not more than 0.3 g.

The preferred mixing ratio is 95%:5% to 85%:15%. The more preferred mixing ratio is 92%:8% to 88%:12% by weight.

In the invention of this application, when we say oxygen-free atmosphere, it means an atmosphere blanketed with an inert gas such as argon.

The particle size of the $Cr-Cr_2O_3$ powder is all right if it does not substantially exceeds $350\mu$ as in the conventionally used oxygen probes. There is no restriction in the filling density.

Now the invention is explained in detail with reference to the attached drawings by way of specific examples and comparative examples.

BRIEF DESCRIPTION OF THE ATTACHED DRAWINGS

FIGS. 1 (a) and (b) are diagrams showing the relation between time and measured emf when oxygen activity in molten steel is measured with conventional oxygen probes. FIG. 1 (a) represents a probe which is poor in response and FIG. 1 (b) represents a probe which is poor in stability.

FIG. 2 is a cross-sectional view of the oxygen probe of embodiments of this invention described hereinafter.

FIGS. 3 (a), (b) and (c) are diagrams showing the relation between time and emf when oxygen activity in a molten steel is measured with oxygen probes in which different reference electrodes are used. FIG. 3 (a) represents a comparative example and FIGS. 3 (b) and (c) represent the reference electrode of this invention.

FIG. 4 is a diagram which shows reproducibility of the reference electrode of Sample 7 by way of the relation of oxygen activity and [% sol.Al]. As a reference, a line representing the theoretical equilibrium of $2Al+3O=Al_2O_3$ is shown, too, therein.

DETAILED DESCRIPTION OF THE INVENTION

Figure 1:
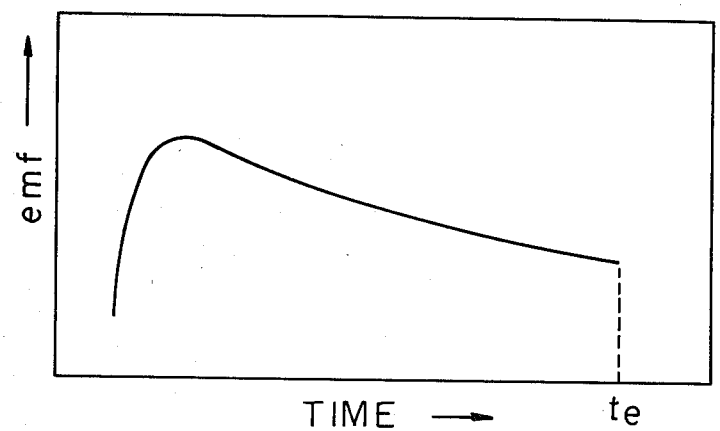
Figure 1:
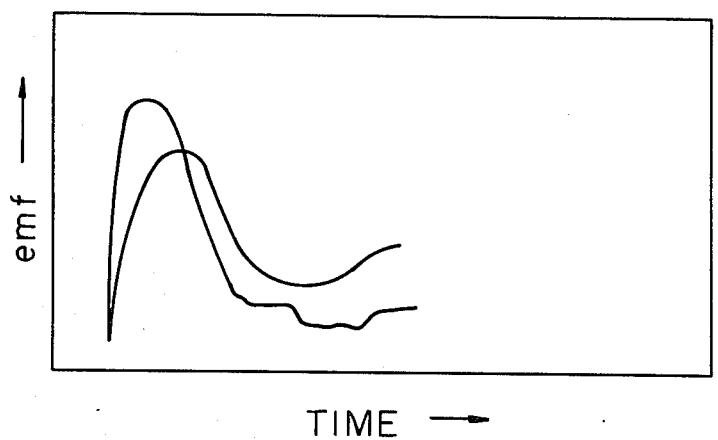

We tested commercially available known oxygen probes. One of them was poor in response. The result is shown in FIG. 1 (a). The emf of this electrode was not stabilized within the allowable immersion time $t_e$, and therefore we had to lift the probe from the molten steel before the emf was stabilized. Another one was poor in stabilization. The result is shown in FIG. 1 (b). This probe did not exhibit a stabilization stage.

We prepared reference electrodes using mixtures of Cr powder and $Cr_2O_3$ powder in various proportions, with varied pre-treatments and varied filling amounts. And we found that the suitable mixing ratio for $Cr/Cr_2O_3$ is 97%:3%–80%:20% by weight, and the preferred pre-treatment is sintering at a temperature not lower than 1550° C. for not less than 3 hours in an oxygen free atmosphere; and the smaller is the filling amount, the more preferred is the probe.

It was known that a mixture of Cr and $Cr_2O_3$ was used as the reference electrode material. But there has been no report on the advantage of sintering the reference electrode material and there has been no evidence that commercially available oxygen probes have sintered $Cr/Cr_2O_3$ reference electrode.

In the invention, if the $Cr_2O_3$ content is less than 3%, the inherent performance of the $Cr/Cr_2O_3$ mixture is lost, and it does not exhibit stable $Cr/Cr_2O_3$ equilibrium oxygen partial pressure. On the other hand, if the $Cr_2O_3$ content is in excess of 20%, the reaction of the oxygen, which is inevitably involved when the electrode is filled, and the metallic Cr is delayed and thus the Cr does not function quickly and steadily as the oxygen catcher.

The untreated Cr/Cr$_2$O$_3$ mixtures are sintered and contract when the electrode is immersed in molten steel, regardless of the Cr/Cr$_2$O$_3$ mixing ratio. Therefore the mixture must be sintered at a temperature not lower than 1550° C., which is the temperature of molten steel.

When quickness of response is considered, the smaller filling amount is preferred. The preferred amount is 0.1–0.3 g.

Figure 2:
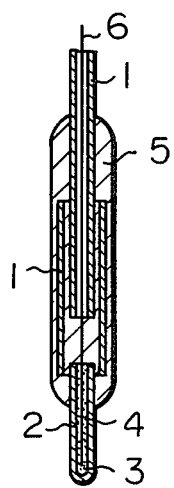

FIG. 2 is a schematic cross-sectional view of the oxygen probes which we used in embodiments of this invention. The probe comprises a Mo lead (6) which is protected by a mullite tube (1) with Al$_2$O$_3$ powder filled therebetween (4) and ends in a Cr/Cr$_2$O$_3$ reference electrode (3); a tube of ZrO$_2$-9% MgO mixture, which is a solid electrolyte, said tube housing the Cr/Cr$_2$O$_3$ reference electrode (3); and Al$_2$O$_3$ cement block (5) which fixes the above-mentioned components. In the illustrated embodiment, the mullite tube comprises two parts. But it can be composed of one part.

Twenty (20) specimens each of 7 different electrodes as indicated in the table below were prepared. The pretreatment was sintering at 1600° C. under Ar atmosphere for 7 hours. The sintered mixtures were pulverized again.

TABLE 1

| Sample No. | Cr/Cr$_2$O$_3$ ratio | Pre-Treatment | Filling Amount (g) | Stability | Response | Reproducibility |
|---|---|---|---|---|---|---|
| 1 | 10/90 | Non-treated | 0.3 | X | — | X |
| 2 | 90/10 | Non-treated | 0.3 | X | — | X |
| 3 | 10/90 | Non-treated | 0.6 | Δ | X | Δ |
| 4 | 90/10 | Non-treated | 0.6 | X | — | X |
| 5 | 10/90 | Treated | 0.6 | X | — | X |
| 6 | 90/10 | Treated | 0.6 | O | Δ | O |
| 7 | 90/10 | Treated | 0.3 | O | O | O |
| 8 | 97/3 | Treated | 0.3 | O | O | O |
| 9 | 80/20 | Treated | 0.3 | O | O | O |
| 10 | 99/1 | Treated | 0.3 | X | — | X |
| 11 | 78/22 | Treated | 0.3 | X | — | X |

O ... Good;
Δ ... Not quite satisfactory;
X ... Unsatisfactory
— ... Unable to be judged because of lingering unstable state.

Figure 3:
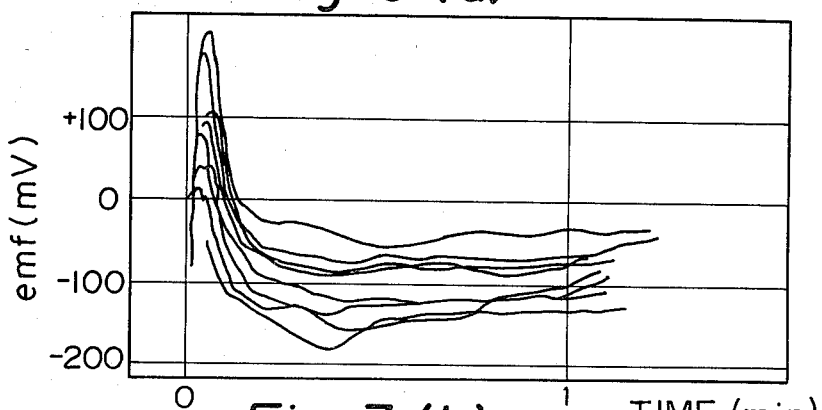
Figure 3:
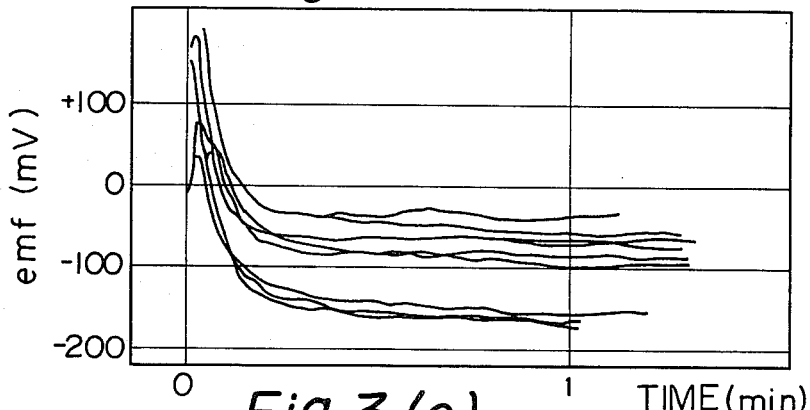
Figure 3:
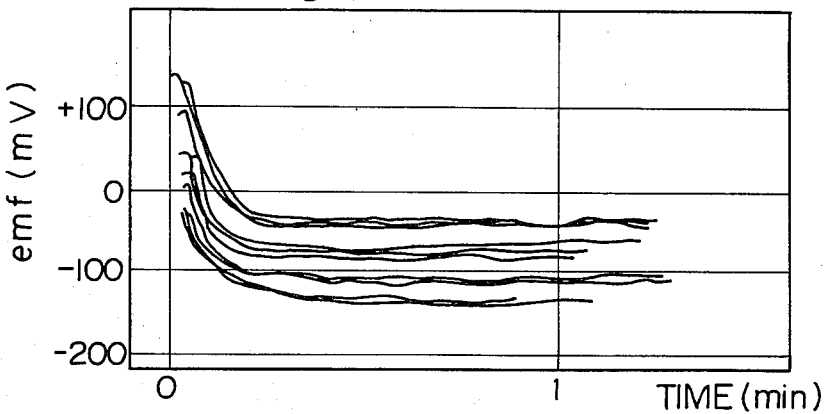

FIGS. 3 (a), (b) and (c) show time-emf curves obtained with respect to typical three of the samples indicated in Table 1. FIG. 3 (a) stands for Sample No. 1, in which the curve shows that the reference electrode is poor in stability and response cannot be judged within the time of testing. The curves for Sample No. 2–No. 4 were almost the same as that for Sample No. 1, and it was learned that reference electrodes made of Cr/Cr$_2$O$_3$ mixtures which had not been sintered are unsatisfactory in stability.

Even when Cr/Cr$_2$O$_3$ mixture is sintered, stability of the electrode is not improved if the proportion of Cr$_2$O$_3$ in the mixture is too great as seen in Sample No. 5.

In contrast, it is learned from FIGS. 3 (b) and (c), which represent Sample No. 6 and No. 7 respectively, that sintering and employment of the claimed mixing ratio in the Cr/Cr$_2$O$_3$ mixture brings about a big improvement in stability. When FIGS. 3 (b) and (c) are compared, however, it is seen that the sample in which a larger amount is filled takes a long time before stabilization, that is, its response is poorer.

Figure 4:
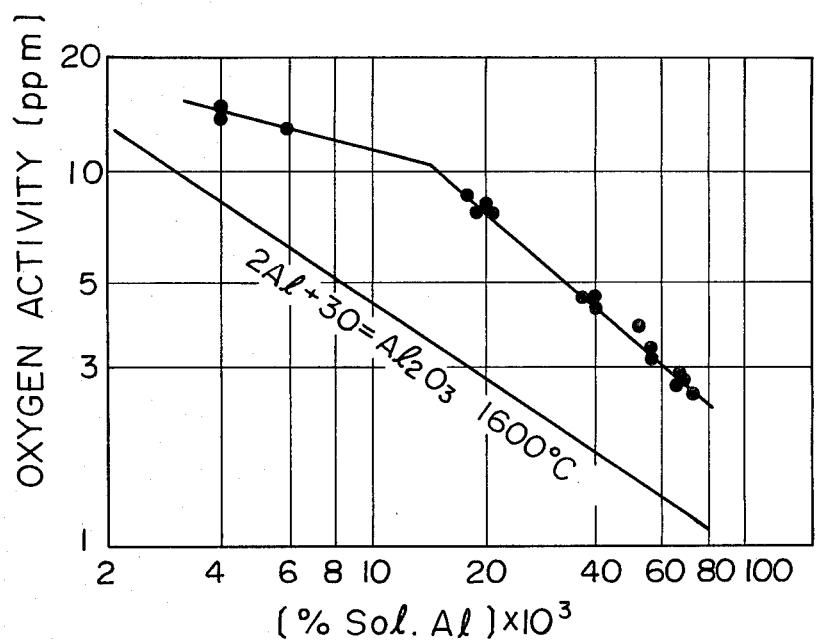

FIG. 4 exhibits reproducibility of Sample No. 7. The curve shows the relation between values of activity of oxygen in molten steel obtained from emf values and molten steel temperatures, and amounts of acid-soluble Al (hereinafter referred to as [% sol.Al]) of molten steel samples taken simultaneously with the measurement of emf. The oxygen activities and the emf values exhibit a definite relation with good reproducibility. Further it should be noted that good reproducibility is exhibited in the oxygen activity range as low as 10 ppm, where measurement with the conventional oxygen probe is problematic.

INDUSTRIAL APPLICABILITY

As has been explained above, the oxygen probe, in which the reference electrode in accordance with this invention is used, is quick in response, excellent in stability and that it has good reproducibility in the lower oxygen range. Therefore, this invention makes possible more precise and effective monitoring and control of molten steel than with prior art probes.

We claim:

1. In a method of making a reference electrode of a mixture of Cr powder and Cr$_2$O$_3$ powder for an oxygen probe, the improvement comprising mixing the Cr powder and Cr$_2$O$_3$ powder in a ratio of 97%:3% to 80%:20% by weight, sintering the mixture at a temperature not lower than 1550° C. in an oxygen free atmosphere and pulverizing said sintered mixture.

2. The improvement of claim 1, said ratio being 95%:5% to 85%:15% by weight.

3. The improvement of claim 2, said ratio being 92%:8% to 88%:12% by weight.

4. The improvement of claim 1, said sintering being for at least three (3) hours.

5. The product made in accordance with the method of claims 1, 2, 3 or 4.

6. In an oxygen probe including a reference electrode formed of a mixture of Cr powder and Cr$_2$O$_3$ powder, the improvement comprising said Cr powder and Cr$_2$O$_3$ powder present in a ratio of 97%:3% to 80%:20% by weight, said powders being presintered at a temperature not lower than 1550° C. in an oxygen free atmosphere and thereafter pulverized to form said mixture.

7. The improvement of claim 6, said Cr-Cr$_2$O$_3$ mixture present in an electrolyte tube in an amount of 0.3 g or less.

8. The improvement of claim 6, said mixture being in a ratio of 95%:5% to 85%:15% by weight.

9. The improvement of claim 8, said mixture being in a ratio of 92%:5% to 85%:15% by weight.

10. The improvement of claims 6, 7 or 8, said powder being presintered for at least 3 hours.

* * * * *